(12) United States Patent
Gerlitz et al.

(10) Patent No.: US 11,141,082 B2
(45) Date of Patent: Oct. 12, 2021

(54) METHOD FOR NON-INVASIVE ANALYSIS OF A SUBSTANCE CONCENTRATION WITHIN A BODY

(71) Applicant: GlucoVista Inc, Fairfield, NJ (US)

(72) Inventors: Yonatan Gerlitz, Herzliya (IL); Alexander Ostritsky, Rishon le Zion (IL)

(73) Assignee: GlucoVista Inc., Fairfield, NJ (US)

(*) Notice: Subject to any disclaimer, the term of this patent is extended or adjusted under 35 U.S.C. 154(b) by 408 days.

(21) Appl. No.: 16/174,168

(22) Filed: Oct. 29, 2018

(65) Prior Publication Data

US 2019/0083014 A1 Mar. 21, 2019

Related U.S. Application Data

(63) Continuation of application No. 12/883,063, filed on Sep. 15, 2010, now abandoned, which is a
(Continued)

(51) Int. Cl.
*A61B 5/1455* (2006.01)
*A61B 5/145* (2006.01)
(Continued)

(52) U.S. Cl.
CPC ........ *A61B 5/14532* (2013.01); *A61B 5/1491* (2013.01); *A61B 5/14546* (2013.01); *A61B 5/01* (2013.01)

(58) Field of Classification Search
CPC .............. A61B 5/1455; A61B 5/14551; A61B 5/14532; A61B 5/14546; A61B 5/1491
See application file for complete search history.

(56) References Cited

U.S. PATENT DOCUMENTS 3,770,958 A 11/1973 Krakow
4,882,492 A 11/1989 Schlager
(Continued)

FOREIGN PATENT DOCUMENTS

EP 0160768 A1 11/1985
EP 0529925 8/1992
(Continued)

OTHER PUBLICATIONS

Office Action issued in Chinese Patent Application No. 201180043984.6 dated Jun. 3, 2014.
(Continued)

*Primary Examiner* — Chu Chuan Liu
(74) *Attorney, Agent, or Firm* — Randall Danskin, P.S.

(57) ABSTRACT

Embodiments of the present methods measure a concentration of a substance, such as glucose, in a body. The described embodiments change the temperature of the surface of a body from a first temperature to a second temperature, then change the temperature of the surface of the body from the second temperature back to the first temperature, and measure a first amount of infrared ("IR") radiation absorbed or emitted from the surface of the body in a first wavelength band, and a second amount of IR radiation absorbed or emitted from the surface of the body in a second wavelength band at predetermined time intervals during the time period that the temperature of the surface of the body changes from the second temperature back to the first temperature. The described embodiments also measure a temperature at the surface of the body and an ambient temperature. A normalized ratio parameter is calculated from the four measurements, and the concentration of the substance in the body is determined by correlating the normalized ration parameter with the body surface temperature and the ambient temperature.

22 Claims, 5 Drawing Sheets

Related U.S. Application Data continuation-in-part of application No. 12/607,903, filed on Oct. 28, 2009, now Pat. No. 8,611,975, and a continuation-in-part of application No. 12/101,859, filed on Apr. 11, 2008, now Pat. No. 8,401,604.

(51) Int. Cl.
*A61B 5/1491* (2006.01)
*A61B 5/01* (2006.01)

(56) References Cited

U.S. PATENT DOCUMENTS

| | | | |
|---|---|---|---|
| 4,883,953 | A | 11/1989 | Koashi et al. |
| 5,191,215 | A | 3/1993 | McClelland et al. |
| 5,237,178 | A | 8/1993 | Rosenthal et al. |
| 5,900,632 | A * | 5/1999 | Sterling ............ A61B 5/14532 250/252.1 |
| 6,198,949 | B1 * | 3/2001 | Braig ................ A61B 5/14532 250/339.03 |
| 6,647,350 | B1 | 11/2003 | Palfenier et al. |
| 7,254,427 | B2 | 8/2007 | Cho et al. |
| 7,521,516 | B2 | 4/2009 | Benson et al. |
| 2002/0133065 | A1 | 9/2002 | Lucassen et al. |
| 2004/0257557 | A1 | 12/2004 | Block |
| 2005/0033186 | A1 | 2/2005 | Nordstrom et al. |
| 2005/0043630 | A1 | 2/2005 | Buchert |
| 2008/0269580 | A1 | 10/2008 | Balistreri et al. |
| 2009/0259407 | A1 | 10/2009 | Gerlitz |

FOREIGN PATENT DOCUMENTS

| | | |
|---|---|---|
| EP | 1568309 A1 | 8/2005 |
| RU | 2122208 | 11/1998 |
| RU | 2376927 | 12/2009 |
| WO | WO1998040723 | 9/1998 |
| WO | WO2000053086 | 9/2000 |
| WO | WO2001030236 | 5/2001 |

OTHER PUBLICATIONS

Office Action issued in Canadian Patent Application No. 2779382 dated May 22, 2014.
Office Action issued in U.S. Appl. No. 13/841,911 dated May 29, 2014.
US Patent and Trademark Office; Final Office Action for U.S. Appl. No. 112/607,903 dated Apr. 30, 2013.
US Patent and Trademark Officel Non-Final Office Action for U.S. Appl. No. 12/607,903 dated Nov. 27, 2012.
US Patent and Trademark Office; Non-Final Office Action for U.S. Appl. No. 12/607,903 dated Jun. 6, 2012.
International Search Report for PCT/US 11/51218 dated Jan. 26, 2012.
International Search Report and Written Opinion of International Application PCT/US2010/050901 dated Mar. 23, 2011.
Patent Examination Report No. 1 for AU Application No. 2010315808, dated Nov. 5, 2012.
Office Action for China Application No. 201080048921.5, dated Feb. 19, 2014.
Office Action for Canada Serial No. 2779382, dated May 22, 2014.
Office Action for U.S. Appl. No. 12/883,063, dated Apr. 4, 2014.
Office Action for China Application No. 201080048921.5, dated Nov. 24, 2014.
Office Action for U.S. Appl. No. 12/883,063, dated May 13, 2015.
Office Action for China Application No. 201080048921.5, dated Jul. 29, 2015.
Communication Pursuant to Article 94(3) EPC, dated Oct. 18, 2017.
Examination Report India Application No. 376CHENP2012, dated Jun. 19, 2018.
Examination Report India Application No. 1990CHENP2013,dated Oct. 17, 2018.

* cited by examiner

METHOD FOR NON-INVASIVE ANALYSIS OF A SUBSTANCE CONCENTRATION WITHIN A BODY

CROSS REFERENCE TO RELATED APPLICATIONS

This application is a continuation of U.S. patent application Ser. No. 12/883,063, entitled "Method for Non-Invasive Analysis of a Substance Concentration Within a Body" and filed on Sep. 15, 2010, which is a continuation-in-part of U.S. patent application Ser. No. 12/607,903, entitled "Apparatus and Method for Non-Invasive Measurement of a Substance Within a Body" and filed on Oct. 28, 2009, and Ser. No. 12/101,859, entitled "Apparatus and Methods for Non-Invasive Measurement of a Substance Within a Body" and filed on Apr. 11, 2008. Each of these applications is incorporated by reference in its entirety herein.

BACKGROUND

The present application relates generally to the non-invasive measurement of various substances in a body, such as the measurement of the concentration of glucose in the human body and, more specifically, to a method employing an electro-optical system to non-invasively analyze the concentration of a substance in a body.

Spectroscopic techniques using infrared ("IR") radiation are known in the prior art and have been widely used for non-invasive measurement of the concentration of substances of interest in a body. One area of particular interest is the use of these techniques for the non-invasive measurement of the concentration of glucose and other constituents of the human bloodstream.

The infrared spectra includes the near infrared (approximately 1 to 3 microns), the middle infrared (approximately 3 to 6 microns), the far infrared (approximately 6 to 15 microns), and the extreme infrared (approximately 15 to 100 microns). Typical prior art glucose and other non-invasive blood constituent measuring devices operate in the near infrared regions where the absorption of infrared energy by glucose and other blood constituents is relatively low. However, it is known that glucose and other blood constituents have strong and distinguishable absorption spectra in both the middle and far infrared regions.

Several patents disclose methods to non-invasively measure the concentration of a substance, such as glucose, for example, in the bloodstream using infrared detection systems and methods. However, none of the disclosed methods consider a method of analysis of the concentration of a substance in a body wherein infrared emissions from a surface of the body are measured in a plurality of time intervals while the temperature of the surface changes from a first temperature to a second temperature.

SUMMARY

The present application discloses a method to analyze and determine, non-invasively, the concentration of a substance in a body. In accordance with one embodiment of the present disclosure, the method comprises the steps of changing the temperature of the surface of a body from a first temperature to a second temperature, then changing the temperature of the surface of the body from the second temperature back to the first temperature. Measuring the infrared radiation absorbed or emitted from the body in a first wavelength band at predetermined time intervals during the change of the temperature of the surface of the body from the second temperature back to the first temperature. Measuring the infrared radiation absorbed or emitted from the body in a second wavelength band at predetermined time intervals during the change of the temperature of the surface of the body from the second temperature to the first temperature. The method further comprises measuring the temperature at the surface of the body, and measuring the ambient temperature. The method further comprises the steps of calculating a normalized ratio parameter based on the IR radiation measured for the first wavelength band, the IR radiation measured for the second wavelength band, the body surface temperature and the ambient temperature, and determining the concentration of the substance in the body by correlating the normalized ratio parameter with the body surface temperature and the ambient temperature. An empirically deprived lookup table may be used to correlate the normalized ratio parameter with the concentration of the substance in the body.

BRIEF DESCRIPTION OF THE DRAWINGS

The following figures, in which like numerals indicate like elements, form part of the present specification and are included to further demonstrate certain aspects of the present disclosure. These embodiments depict the novel and non-obvious aspects of the disclosure shown in the accompanying drawings, which are for illustrative purpose only. The disclosure may be better understood by reference to one or more of these figures in combination with the detailed written description of specific embodiments presented herein.

These and other embodiments of the present application will be discussed more fully in the description. The features, functions, and advantages can be achieved independently in various embodiments of the present disclosure, or may be combined in yet other embodiments.

DETAILED DESCRIPTION

Embodiments of the present disclosure provide methods to non-invasively analyze and measure the concentration of a substance in a body. In certain embodiments, the analyzed substance may be glucose in the human bloodstream. However, those of ordinary skill in the art will appreciate that the present methods may be used to analyze and measure concentrations of other substances as well, such as cholesterol, for example.

Figure 1:
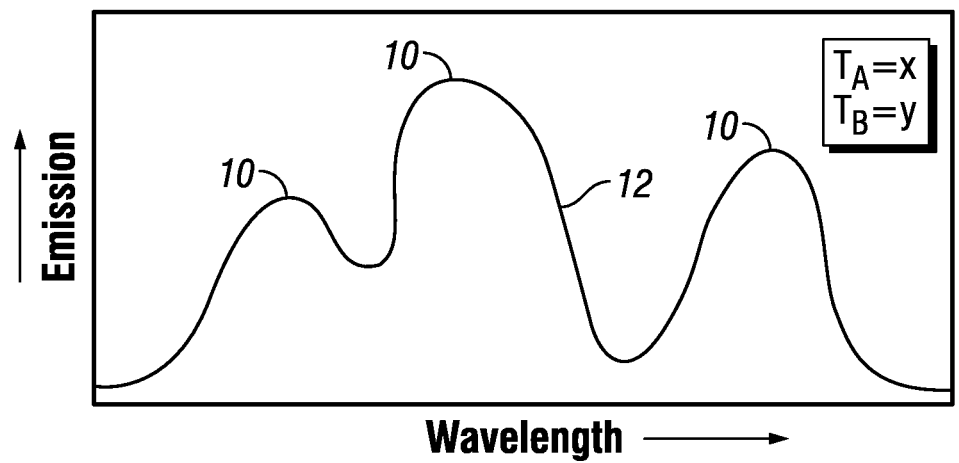
FIG. 1 is a plot of infrared radiation emitted from and absorbed by a hypothetical body across a given spectrum.

All bodies and all substances absorb and emit infrared ("IR") radiation. The magnitude of IR radiation absorbed or emitted at a given wavelength varies as a function of the body's temperature and the ambient temperature. FIG. 1 illustrates a sample plot of the IR radiation emission spectrum for a hypothetical body, where the ambient temperature $T_A$ is equal to x and the body temperature $T_B$ is equal to y. As shown, for a given ambient temperature and body temperature, a body more readily emits and absorbs IR radiation at certain wavelengths, represented by the peaks 10 in the spectrum shown by curve 12.

The IR spectra includes the near infrared (approximately 1 to 3 microns), the middle infrared (approximately 3 to 6 microns), the far infrared (approximately 6 to 15 microns), and the extreme infrared (approximately 15 to 100 microns). In certain substances IR absorption/emission is particularly distinctive in the far infrared ("FIR") spectrum. For example, it is known that glucose and other blood constituents have strong and distinguishable absorption spectra in both the middle and far infrared regions. Thus, to measure the concentration of substances such as glucose, for example, in a body, it is advantageous to measure the FIR radiation emitted by the body.

Embodiments of the present methods measure the FIR radiation absorbed or emitted by a body at different wavelength bandwidths or bands. The first wavelength band (or bands) is selected to be in a band (or bands) where the substance of interest is known to have significant absorption/emission characteristics. The second wavelength band (or bands) is selected to be in a band (or bands) where the substance is known to have no or negligible absorption/emission. In an alternate embodiment, the second wavelength band (or bands) is selected to be the entire FIR absorption/emission spectrum of the body.

Figure 2:
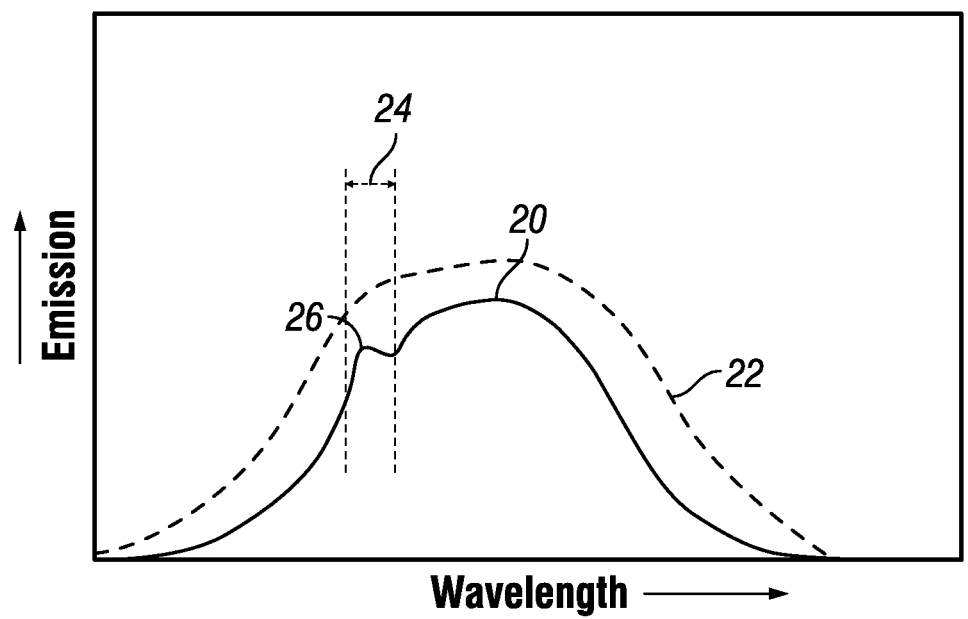
FIG. 2 is a plot of far infrared radiation emitted from and absorbed by a hypothetical body and a blackbody across a given spectrum.

In some embodiments, the FIR measurements are normalized against a blackbody. A blackbody, as those of ordinary skill in the art will appreciate, is one that absorbs and emits radiation with a theoretical emissivity of one. FIG. 2 illustrates a sample plot of the FIR absorption/emission spectrum for a hypothetical body (solid curve 20) and for a blackbody (dashed curve 22). For both the body and the blackbody the ambient temperature $T_A$ is the same. Similarly, for both the body and the blackbody the body temperature $T_B$ is the same for each set of measurements. The dashed vertical lines define a first wavelength band 24 in which the substance whose concentration is to be measured is known to have an FIR absorption/emission peak 26. For example, for glucose, the selected band 24 may be between about 9.3 microns and about 9.9 microns.

In one embodiment of the present disclosure, to analyze and measure a substance concentration, the temperature of an area of the surface of a body, an area of skin on a human body, for example, is changed from a first temperature to a second temperature for a period of time (i.e., as by heating or cooling), and then allowed to recover or revert from the second temperature to the first temperature over a period of time. During the recovery of the surface temperature of the body, the IR radiation from the surface of the body is measured both in the wavelength bandwidth for the substance of interest and in the wavelength bandwidth not including the wavelength of the substance of interest at each of a plurality of predetermined time intervals. The results of the measurements are plotted as a function of elapsed time versus temperature of the surface in two curves, one for the wavelength bandwidth of interest and one for the wavelength bandwidth not including the wavelength of interest.

The difference between the two curves or functions due to the contribution of the IR wavelength emission/absorption of the substance of interest in the body can be analyzed by calculating the value of the functions for the two curves at each of the measurement times or by determining the difference between the constants for each of the two curves. The average ratio of the two radiation measurements after normalization for a black body reading is correlated to the concentration of the desired substance in the body, such as the concentration of glucose in the bloodstream of a human body, for example.

Figure 3:
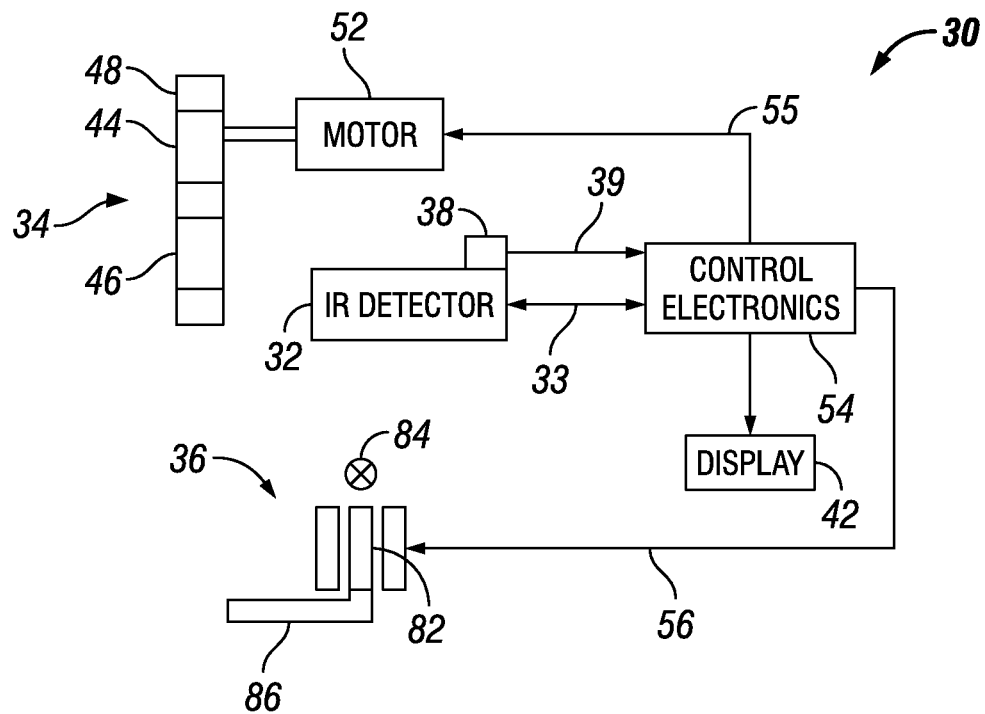
FIG. 3 is a block diagram illustrating one embodiment of a system for the non-invasive measurement of the concentration of a substance in a body.

Referring now also to FIG. 3, a block diagram of a system 30 for the non-invasive measurement of the concentration of a substance in a body is shown. Broadly, the illustrated embodiment of the present system 30 comprises an infrared ("IR") radiation detector 32, an IR filter assembly 34, heating and/or cooling apparatus 36, and apparatus 38 for measuring the ambient temperature. In some embodiments, the IR detector 32 measures the body surface temperature.

In one embodiment, the IR detector 32 may comprise a thermopile with collimating optics. However, those of ordinary skill in the art will appreciate that the IR detector 32 may comprise a different type of detector, such as a bolometer, for example. The system 30 shown in FIG. 3 further comprises a display 42 for presenting information such as the substance concentration, the measured parameters and other information of interest. In certain embodiments, the display 42 may comprise a liquid crystal display ("LCD").

With continued reference to FIG. 3, the IR filter assembly 34 is positioned between the body and the IR detector 32. In the illustrated embodiment, the IR filter assembly 34 comprises two filters 44, 46, although those of ordinary skill in the art will appreciate that the IR filter assembly 34 may include any number of filters. A first filter, filter 44, for example, will preferably be a narrow band filter passing the wavelengths of the spectral characteristic of the substance being measured. A second filter, filter 46, for example, will preferably be a narrow band filter passing those wavelengths of a spectral characteristic not sensitive to the substance being measured. For example, in some embodiments, filter 46 will limit the bandwidth to that region of the spectrum where there is no emission for the substance being measured (for glucose, for example, the bandwidth may be 10.5μ-15μ), while filter 44 would have a bandwidth characteristic of the emission of the substance being measured (for glucose, for example, the bandwidth may be 8.5μ-10.5μ). In some embodiments, the second filter 46 may transmit, for example, all of the IR radiation between approximately 7 microns and approximately 15 microns.

In the illustrated embodiment, the system 30 includes a drive motor 52. In certain embodiments, the drive motor 52 may comprise a solenoid. The drive motor 52 is configured to provide a motive force for changing a position of the filter assembly 34 with respect to the IR detector 32. Activation of the drive motor 52 enables the filters 44, 46 to be sequentially positioned between the body and the IR detector 32 as each IR radiation measurement is taken.

Figure 4:
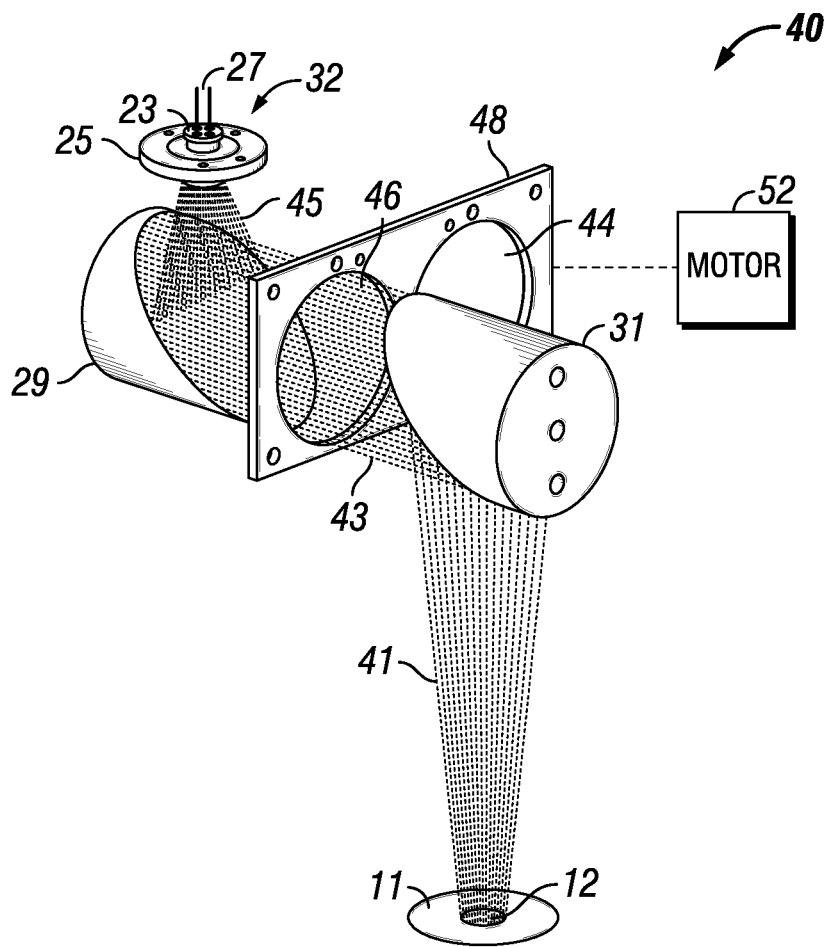
FIG. 4 is a perspective view of the optical and detector apparatus of FIG. 3 illustrating the path of travel for electromagnetic rays between the body and the detector.

Referring now also now also to FIG. 4, a schematic perspective view is shown of the configuration of an optical subsystem 13 and IR detector 32 components of the system 30 shown in FIG. 3, illustrating the path of travel for IR radiation rays between a body 11 and the detector 32. The detector 32 includes a detector element 23, detector base 25 and detector leads 27. The configuration of the optical and detector components is designed such that an image 12 of the sensitive or active area 47 of the detector 15 is created at the body 11 on the focal plane of mirror 31.

In some embodiments, the area of image 12 at the surface of body 11 preferably has a diameter of approximately 6 mm. IR radiation emitted from or reflected by the body 11 at image 12 in beam 41 is collected and collimated by mirror 31. The IR radiation is reflected by mirror 31 and propagated to mirror 29 in a collimated beam 43 of parallel rays via filter 44 or filter 46. The focal plane of mirror 29 is located at the surface of a sensitive area of the IR detector 32. The beam 43 reaching mirror 29 is reflected and propagated as beam 45 and focused at the focal plane of mirror 29 incident on the IR detector 32 sensitive area.

Thus, the optical subsystem 13 is aligned such that the image 12 is positioned at the surface of body 11 and the beam 41 of IR radiation is incident on the sensitive area of IR detector 32 via mirror 31, filter 33 or filter 35 and mirror 29.

In one embodiment, mirrors 29 and 31 are preferably ninety-degree (90°) off-axis parabolic mirrors coated with gold or other suitable reflective material. Preferably mirror 29 will have a focal length of about one (1) inch and mirror 31 will have a focal length of about three (3) inches. Other suitably designed reflective mirrors may be used for the optical subsystem 13 such as ellipsoid mirrors or a combination of ellipsoid and hyperbolic mirrors, for example.

Filter 44 and filter 46 are mounted in frame 48, frame 48 being positioned between mirror 29 and mirror 31. The filters 44, 46 are switched between positions intercepting the beam 43 using a suitable driving mechanism, such as a motor or pneumatic pressure, for example, coupled to frame 48. In one embodiment, motor 52 is coupled to the frame 48 and positions the frame 48 between the mirror 29 and mirror 31 such that the desired filter 44, 46 intercepts the beam 43.

Figure 5:
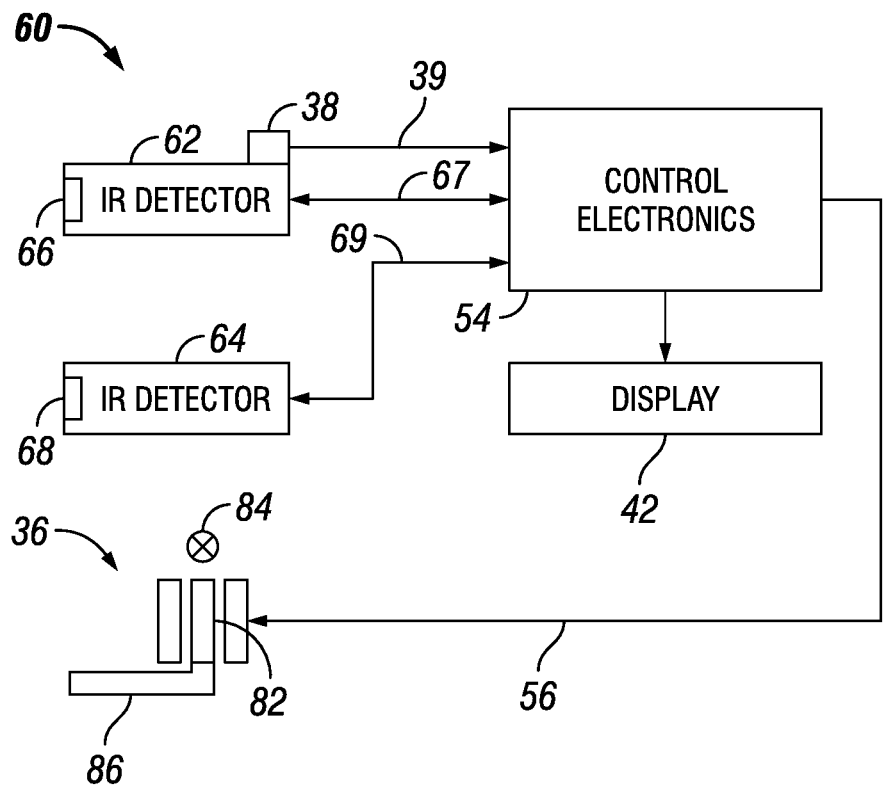
FIG. 5 is a block diagram illustrating another embodiment of a system for the non-invasive measurement of the concentration of a substance in a body.

Referring now also to FIG. 5, a block diagram of an alternative embodiment of the present system 60 is shown. In the system 60, the drive motor 52 and the filter assembly 34 are replaced with a plurality of fixed position IR detectors. In the illustrated embodiment, two IR detectors 62, 64 are shown. However, those of ordinary skill in the art will appreciate that any number of IR detectors may be provided. In the embodiment of FIG. 5, each IR detector 62, 64 includes its own IR filter 66, 68, respectively. The filters 66, 68 may, for example, be substantially similar to the two filters 44, 46 provided in the embodiment of FIG. 3 with respect to the wavelengths of IR radiation each filter transmits. In the embodiment of FIG. 5, there are advantageously no moving parts in the detector/filter assembly, and all measurements may be taken simultaneously.

With continuing reference to FIGS. 3 and 5, the illustrated embodiments of the present system, 30, 60 include apparatus 38 for measuring the ambient temperature. In certain embodiments, the ambient temperature measuring apparatus 38 may comprise a thermistor, such as a negative temperature coefficient thermistor. For simplicity, the ambient temperature measuring apparatus 38 will be referred to as thermistor 38. However, those of ordinary skill in the art will appreciate that the ambient temperature measuring apparatus 38 may be any apparatus that is suitable for measuring the ambient temperature, such as a thermocouple, for example. While in the illustrated embodiments, the thermistor 38 is shown attached to the IR detectors 32 and 62, 64, those of ordinary skill in the art will appreciate that it need not be. In certain embodiments, the thermistor 38 measures the temperature of a housing (not shown) of the IR detectors 32 and 62, 64 which is typically equal to the ambient temperature.

Figure 6:
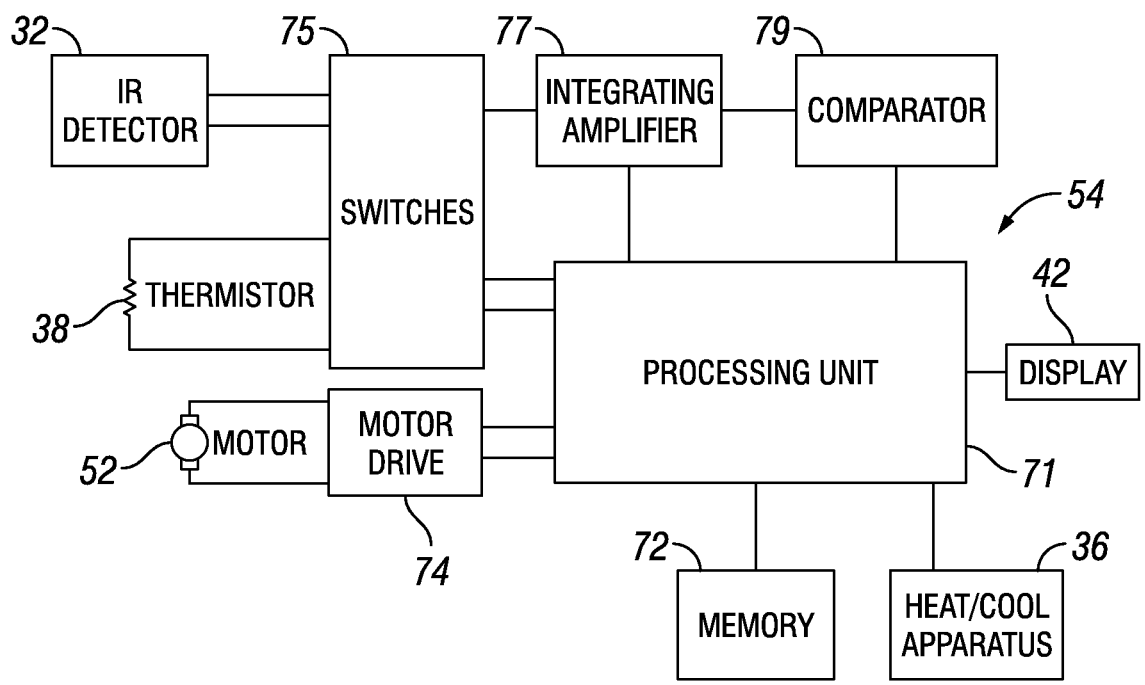
FIG. 6 is a block diagram illustrating the control electronics for the systems illustrated in FIGS. 3 and 5.

Referring now also to FIG. 6, a block diagram illustrating the control electronics for the systems illustrated in FIGS. 3 and 5 is shown. Outputs 33 and 67, 69 of the IR detector(s) 32 and 62, 64, the thermistor 38 output 39, and control inputs 55, 56 of the drive motor 52 and the heating/cooling apparatus 36, respectively, are connected to control electronics 54. FIG. 6 illustrates further details of the control electronics 54, which include a processing unit 71 and memory 72. The memory 72 may include one or more lookup tables for calculating and determining results of the measurements taken by the present system 30, 60. For example, the memory 72 may include an empirically derived lookup table that correlates a normalized ration parameter with the concentration of the substance of interest in the body. One example of an empirically derived lookup table is described in pending U.S. patent application Ser. No. 12/101,859, incorporated by reference in its entirety herein. The processing unit 71 may comprise a central processing unit ("CPU") running software and/or firmware. Alternatively, the processing unit 71 may comprise one or more application-specific integrated circuits ("ASIC"). The processing unit 71 also drives the display 42 to display results that may include the substance concentration, the measurements taken by the IR detectors 32 and 62, 64 and/or the thermistor 38, and other information of interest. In the embodiment of FIG. 6, the processing unit 71 also controls a motor drive 74, which in turn controls the drive motor 52 to change the position of the filter assembly 34 with respect to the IR detector 32.

With continuing reference to FIG. 6, the illustrated control electronics 54 include one or more switches 75 for switching between measurement channels. For example, the switches 75 might change between a first channel that carries a signal from the IR detector 32 or IR detectors 62, 64 and a second channel that carries a signal from the thermistor 38. The processing unit 71 controls the switches 75.

The illustrated control electronics 54 further include an integrating amplifier 77. The integrating amplifier 77 amplifies a voltage generated by the IR detector 32 or IR detectors 62, 64 to a measurable value. The voltage generated by the IR detector 32 or IR detectors 62, 64 is proportional to the detected body IR radiation, and may be very small. The illustrated control electronics 54 further includes a comparator 79. The comparator 79, together with the integrating amplifier 77, converts the voltage from the IR detector 32 or IR detectors 62, 64 into a time interval that is inversely proportional to the input voltage and is measured by the processing unit 71.

With continuing reference to FIGS. 4 and 5, in certain embodiments the heating/cooling apparatus 36 comprises a Peltier element 82 configured to provide a desired amount of heat or cold, a fan 84 to drive the heated or cooled air, and a funnel 86 to direct the heated or cooled air onto the body surface. However, those of ordinary skill in the art will appreciate that the heat/cooling apparatus 36 may be any apparatus that is suitable for this purpose.

Applying heat or cold to the body (skin) surface stimulates the absorption or emission of IR radiation by the substance whose concentration is to be measured. In the case of glucose, for example, cooling the skin stimulates the absorption of IR radiation while heating the skin stimulates the emission of IR radiation. The heating/cooling apparatus 36 heats or cools the surface area of the body from a first temperature to a second temperature and maintains the surface area at the second temperature for a predetermined amount of time. The heating/cooling apparatus 36 may also be utilized to heat or cool the surface area to change the temperature of the surface from the second temperature to the first temperature, or an intermediate temperature, at a controlled rate.

Figure 7:
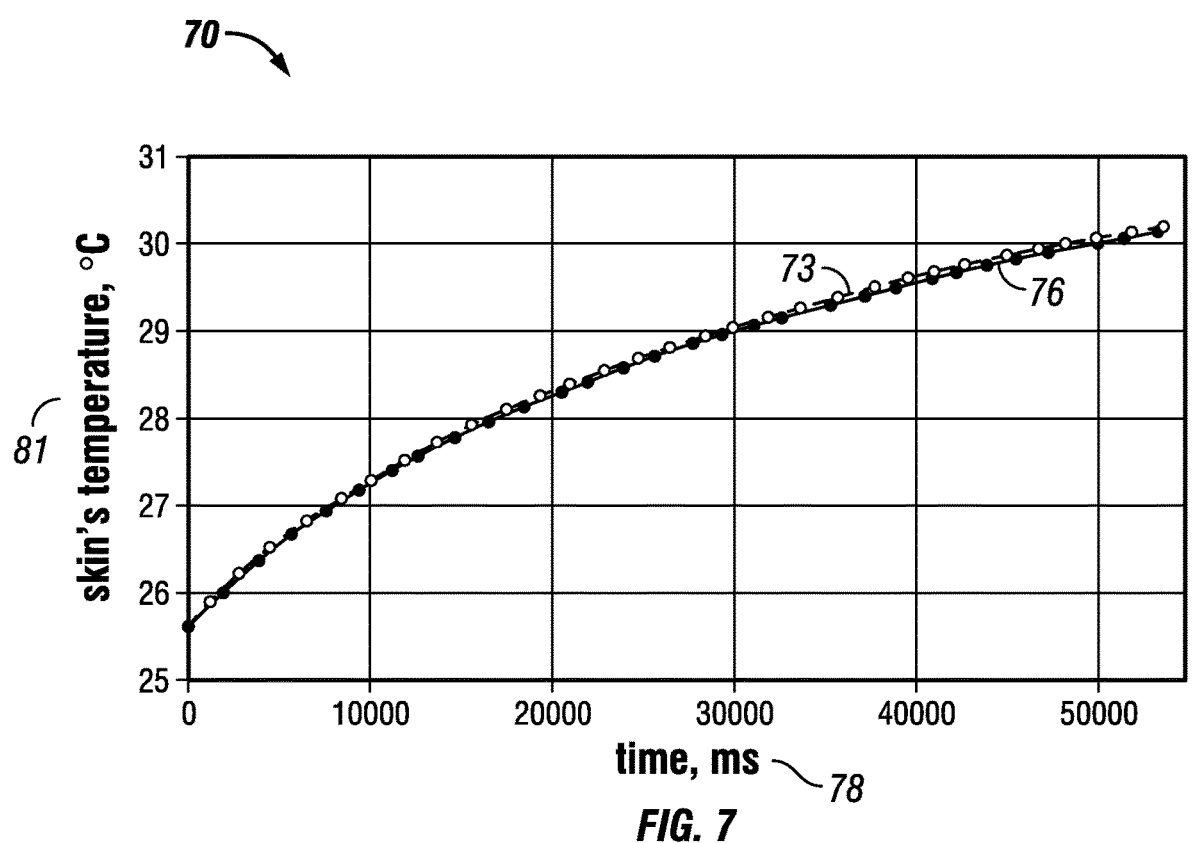
FIG. 7 is a graph illustrating the temperature recovery function of the human skin as measured with the optical and detector system of FIGS. 3, 4 and 5.

Referring now also to FIG. 7, a graph illustrating the temperature recovery function of the surface of a body as measured with the optical and detector system of FIGS. 3, 4 and 5 is shown. The graph 70 shown in FIG. 7 illustrates the temperature recovery function of the human skin as measured with an electro-optical system employing two IR filters. The upper curve 73 describes the function of the recovery of the skin's temperature from a second temperature to a first temperature as measured with a filter for a first wavelength band where the substance of interest has a strong absorption/emission characteristic. The lower curve 76 describes the function of the recovery of the skin's temperature from a second temperature to a first temperature as measured with a filter for a second wavelength band where the substance of interest has no or a negligible absorption/emission characteristic.

Alternatively, the lower curve 76 could describe the function of the recovery of the skin's temperature from a second temperature to a first temperature as measured with a filter for the entire FIR wavelength band including both a wavelength band where the substance of interest has a strong absorption/emission characteristic as well as the remaining wavelength band where the substance of interest has no or a negligible absorption/emission characteristic. The IR radiation measurements taken by the IR detector 32 or the detectors 62, 64 are plotted as a function of the temperature of the surface of the body versus the elapsed time when the temperature of the surface begins to change back to a first temperature from a second temperature.

Figure 8:
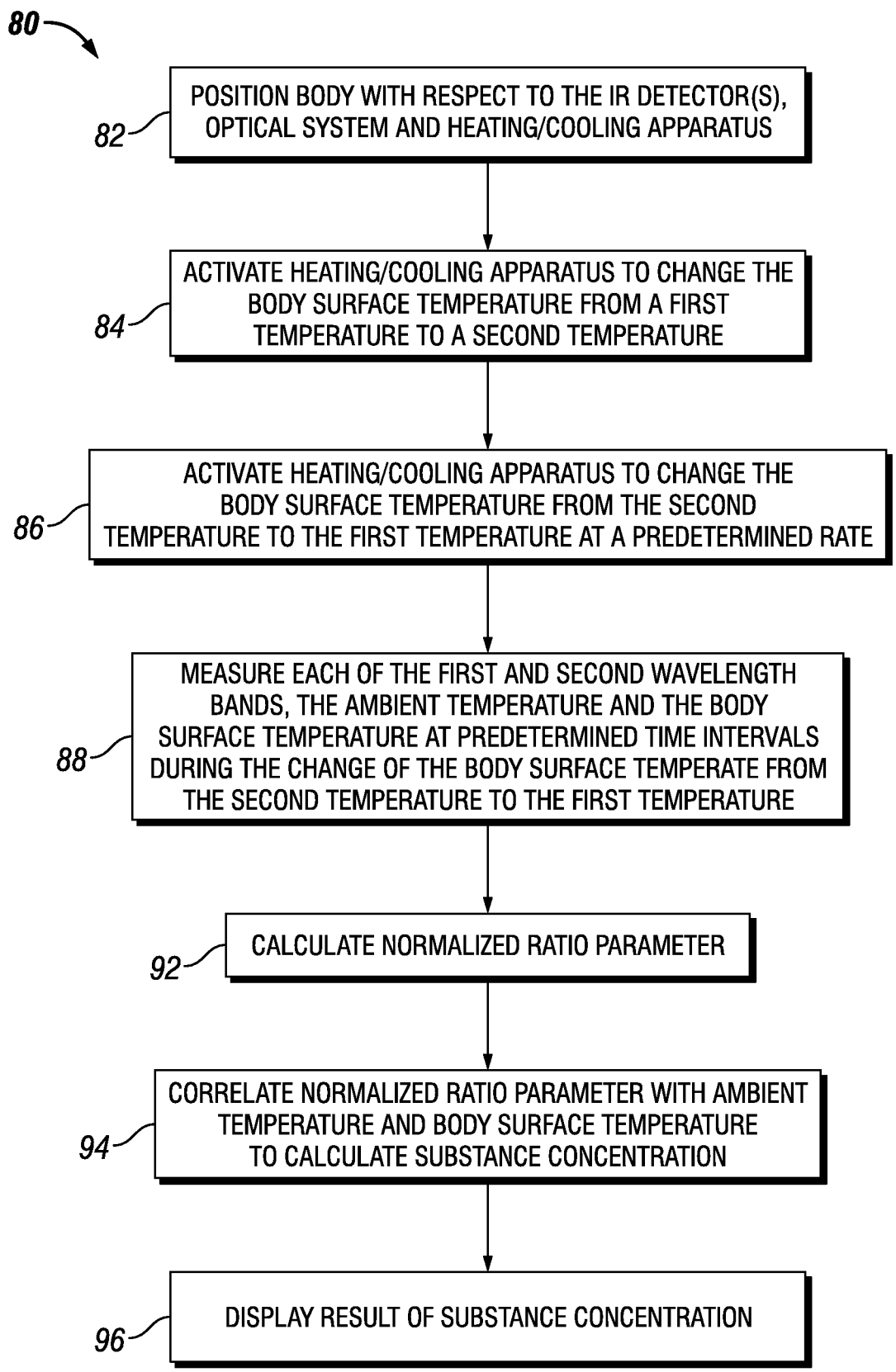
FIG. 8 is a process flow chart illustrating one embodiment of the present method for analyzing a concentration of a substance in a body.

Referring now also to FIG. 8, the process flowchart 80 illustrates one embodiment of a method for measuring the concentration of a substance within a body. At step 82, the IR radiation detector(s) 32 or 62, 64 and the heating/cooling apparatus 36 are positioned with respect to the body surface. At step 84, the heating/cooling apparatus 36 is activated to heat (or cool) the temperature of the body surface area, such as image area 12 (as shown in FIG. 4), for example, to change the surface area from a first temperature to a second temperature. The temperature of the body surface area is then held at the second temperature for a predetermined period of time. At step 86, the heating/cooling apparatus 36 is activated to cool (or heat) the body surface area to change the surface area from the second temperature back to the first temperature at a predetermined rate. Alternatively, air at an ambient temperature may be used to cool (or heat) the body surface area to change the temperature of the body surface area from the second temperature back to the first temperature.

At step 88, the absorption/emission of IR radiation over each of the first and second wavelength bands, the ambient temperature and the body surface temperature are measured at predetermined time intervals as the temperature of the body surface area changes back to the first temperature from the second temperature. In the embodiment of the present system illustrated in FIGS. 3 and 4, measurement of the IR radiation in both the first and second wavelengths is accomplished by switching between the two filters 44, 46 at each of the predetermined time intervals. In the embodiment of the present system illustrated in FIG. 5, all of the measured parameters including the IR radiation in both the first and second wavelength bands can be measured simultaneously. At step 92, the normalized ratio parameter is calculated from the IR radiation measurements. At step 94, the normalized ratio parameter is correlated with the ambient temperature and the body surface temperature using a lookup table. At step 96, the substance concentration is displayed.

With either embodiment of the system 30, 60 shown in FIGS. 3 and 5, an alternative method of measuring the absorption/emission of IR radiation, the ambient temperature and the body surface temperature is to first scan the body surface while taking multiple measurements at various points on the body surface to determine the most desirable location on the surface of the body to measure the concentration of the substance. Software, for example, may be used to identify the most desirable location on the surface of the body from the plurality of measurements taken during the body scan. Parameters for selecting the most desirable location may be, for example, repeatability, maximum signal strength, and the like.

The above description presents the best mode contemplated for carrying out the present methods for non-invasive analysis of a substance concentration within a body, and of the manner and process of practicing them, in such full, clear, concise, and exact terms as to enable any person skilled in the art to which they pertain to practice these methods. These methods are, however, susceptible to modifications and alternate constructions from those described above that are fully equivalent. Consequently, these methods are not limited to the particular embodiments disclosed herein. On the contrary, these methods cover all modifications and alternate constructions coming within the spirit and scope of the methods as generally expressed by the following claims, which particularly point out and distinctly claim the subject matter of the methods.

What is claimed is:

1. A method comprising:
decreasing a temperature of a surface of a body from a first temperature to a second temperature less than the first temperature using a heating/cooling apparatus;
thereafter, recovering to the first temperature by increasing the temperature of the surface of the body from the second temperature to the first temperature using the heating/cooling apparatus or without the use of any heating apparatus;
measuring a first amount of infrared radiation absorbed or emitted from the body in a first wavelength band at predetermined time intervals during the recovery increasing the surface of the body from the second temperature to the first temperature using an infrared (IR) radiation detector, the first wavelength band being a wavelength band or bands in which a substance in the body emits or absorbs infrared radiation;
measuring a second amount of infrared radiation absorbed or emitted from the body in a second wavelength band at predetermined time intervals during the recovery increasing the surface of the body from the second temperature to the first temperature using the IR radiation detector or another IR radiation detector;
measuring a temperature of the surface of the body using the IR radiation detector or a body surface temperature sensor;
measuring an ambient temperature using a thermistor, a thermocouple, or an ambient temperature sensor;
calculating a normalized ratio parameter based on the first amount, the second amount, the body surface temperature, and the ambient temperature; and
determining a concentration of a substance in the body non-invasively by using a correlation with the normalized ratio parameter.

2. The method of claim 1, wherein the second wavelength band is the entire spectrum in which the body emits or absorbs infrared radiation in the far infrared spectrum.

3. The method of claim 1, wherein the second wavelength band is the entire spectrum in which the substance has no or negligible emission and absorption of infrared radiation.

4. The method of claim 1, wherein the normalized ratio parameter is the average ratio selected from the group consisting of at least one of the ratio of the first amount normalized against a black body to the second amount normalized against a black body at each time interval, and a logarithm of the ratio of the first amount normalized against a black body to the second amount normalized against a black body at each time interval.

5. The method of claim 1, wherein the substance is glucose.

6. The method of claim 1, wherein the body is a human body.

7. The method of claim 1, wherein the concentration of the substance in the body is determined using an empirically derived lookup table.

8. The method of claim 1 wherein the first wavelength band comprises about 8.5μ to about 10.0μ and the second wavelength band comprises about 7.0μ to about 15.0μ.

9. The method of claim 8 wherein the second wavelength band comprises about 10.5μ to about 15.0μ.

10. The method of claim 1 wherein the step of increasing the temperature of the surface of the body from the second temperature to the first temperature is at a predetermined rate.

11. A method comprising:
using an apparatus including an infrared (IR) radiation detector and an optical system;
decreasing a temperature of a surface of a body from a first temperature to a second temperature less than the first temperature using a heating/cooling apparatus;
thereafter, recovering to the first temperature by increasing the temperature of the surface of the body from the second temperature to the first temperature using the heating/cooling apparatus or without the use of any heating apparatus;
detecting an infrared radiation value emitted by the body in a wavelength band including at least one wavelength characteristic of a substance in the body at predetermined time intervals during the recovery increasing the surface of the body from the second temperature to the first temperature using the IR radiation detector;
limiting, using the optical system, the wavelength range of the detected infrared radiation to a first wavelength band including the at least one wavelength characteristic of the substance to provide the detected radiation value;
detecting another infrared radiation value emitted by the body in another wavelength band at predetermined time intervals during the recovery increasing the surface of the body from the second temperature to the first temperature using the IR radiation detector or another IR radiation detector; and
using the detected infrared radiation value and the other detected infrared radiation value, noninvasively measuring a concentration of the substance in the body.

12. The method of claim 11, further comprising the step of measuring the ambient temperature using a thermistor, a thermocouple, or an ambient temperature sensor, the measurement of concentration further including using the ambient temperature.

13. The method of claim 12, further comprising the step of measuring the temperature of the body using the IR radiation detector or a body surface temperature sensor, the measurement of concentration further including using both the ambient and body temperature.

14. The method of claim 11, furthering comprising the step of limiting, using the optical system, the wavelength band of the other detected infrared radiation.

15. The method of claim 14, further comprising the step of limiting, using the optical system, the wavelength range of the other detected infrared radiation to a second wavelength band wherein wavelengths characteristic of the substance are negligible to provide the other detected radiation value.

16. The method of claim 15, wherein the first wavelength band comprises about 8.5μ to about 10.0μ and the second wavelength band comprises about 7.0μ to about 15.0μ.

17. The method of claim 16 wherein the second wavelength band comprises about 10.5μ to about 15.0μ.

18. The method of claim 11 wherein the step of increasing the temperature of the surface of the body from the second temperature to the first temperature is at a predetermined rate.

19. A method comprising:
decreasing a temperature of a surface of a body from a first temperature to a second temperature less than the first temperature using a heating/cooling apparatus;
thereafter, recovering to the first temperature by increasing the temperature of the surface of the body from the second temperature to the first temperature using the heating/cooling apparatus or without the use of any heating apparatus;
measuring a first amount of infrared radiation absorbed or emitted from the body in a first wavelength band of the spectrum between 6 and 15 microns at predetermined time intervals during the recovery increasing the surface of the body from the second temperature to the first temperature using an infrared (IR) radiation detector, the first wavelength band being selected wherein a substance of interest exhibits absorption/emission characteristics;
measuring a second amount of infrared radiation absorbed or emitted from the body in a second wavelength band at predetermined time intervals during the recovery increasing the surface of the body from the second temperature to the first temperature using the IR radiation detector or another IR radiation detector, the second wavelength band being different from the first wavelength band and including wavelengths in which the substance exhibits no or negligible absorption/emission characteristics;
measuring a temperature of the surface of the body using the IR radiation detector or a body surface temperature sensor;
measuring an ambient temperature using a thermistor, a thermocouple, or an ambient temperature sensor;
calculating a normalized ratio parameter based on the first amount, the second amount, the body surface temperature, and the ambient temperature, the normalized ratio parameter being the average ratio selected from the group consisting of at least one of the ratio of the first amount normalized against a black body to the second amount normalized against a black body at each time interval, and a logarithm of the ratio of the first amount normalized against a black body to the second amount normalized against a black body at each time interval; and determining a concentration of the substance in the body non-invasively by using an empirically-derived lookup table including a correlation with the normalized ratio parameter.

20. The method of claim 19 wherein the first wavelength band comprises about 8.5μ to about 10.0μ and the second wavelength band comprises about 10.5μ to about 15.0μ.

21. The method of claim 19 further comprising:
using an apparatus including the IR radiation detector and an optical system;
aligning the optical system to position an image of a sensitive area of the detector at a focal plane coinciding with the surface of the body; and
receiving the first and second amounts of infrared radiation through the aligned optical system to the IR radiation detector.

22. A method comprising:
decreasing a temperature of a surface of a body from a first temperature to a second temperature less than the first temperature using a heating/cooling apparatus;
thereafter, recovering to the first temperature by increasing the temperature of the surface of the body from the second temperature to the first temperature using the heating/cooling apparatus or without the use of any heating apparatus;
measuring a first amount of infrared radiation absorbed or emitted from the body in a first wavelength band at predetermined time intervals during the recovery increasing the surface of the body from the second temperature to the first temperature using an infrared (IR) radiation detector, a substance of interest exhibiting absorption or emission in the first wavelength band;
generating a first signal having a first radiation measurement value indicative of the first amount;
measuring a second amount of infrared radiation absorbed or emitted from the body in a second wavelength band different from the first wavelength band at predetermined time intervals during the recovery increasing the surface of the body from the second temperature to the first temperature using the IR radiation detector or another IR radiation detector, the second wavelength band including wavelengths in which the substance exhibits no or negligible absorption and emission;
generating a second signal having a second radiation measurement value indicative of the second amount;
measuring a temperature of the surface of the body using the IR radiation detector or a body surface temperature sensor;
generating a third signal having a third value indicative of the temperature of the surface;
measuring an ambient temperature using a thermistor, a thermocouple, or an ambient temperature sensor;
generating a fourth signal having a fourth value indicative of the ambient temperature;
using a memory device configured to store (a) ambient temperature values, (b) body surface temperature values, and an empirically-derived look-up table containing data correlating values for a concentration of the substance in the body with (c) normalized ratio parameter values, each of which is determined by the ratio of (1) a radiation measurement value in the first wavelength band normalized against a first blackbody reading in the first wavelength band to (2) a radiation measurement value in the second wavelength band normalized against a second blackbody reading in the second wavelength band, or each of which is determined by a logarithm of the ratio of (1) to (2);
using a processor configured to receive the first, second, third, and fourth signals, the processor being operably associated with the memory device so as to access the lookup table therefrom;
operating the processor to normalize the first radiation measurement value against the first blackbody reading and to normalize the second radiation measurement value against the second blackbody reading;
operating the processor to calculate a normalized ratio parameter value as the ratio of the normalized first radiation measurement value to the normalized second radiation measurement value and to correct the normalized ratio parameter value using the body surface temperature third value and the ambient temperature fourth value to obtain a corrected normalized ratio parameter value;
operating the processor to calculate an average of corrected normalized ratio parameter values determined during the recovery increasing the surface of the body from the second temperature to the first temperature; and
operating the processor to determine a concentration of the substance in the body non-invasively by using the empirically-derived lookup table including a correlation with the average corrected normalized ratio parameter value.

* * * * *